United States Patent
Holvey et al.

(10) Patent No.: US 7,370,349 B2
(45) Date of Patent: May 6, 2008

(54) METHOD AND SYSTEM FOR PROTECTING INFORMATION ON A COMPUTER SYSTEM

(75) Inventors: R David Holvey, Pacifica, CA (US); Arthur Douglas Jopling, San Rafael, CA (US)

(73) Assignee: PeopleChart Corporation, San Francisco, CA (US)

( * ) Notice: Subject to any disclaimer, the term of this patent is extended or adjusted under 35 U.S.C. 154(b) by 125 days.

(21) Appl. No.: 10/655,243

(22) Filed: Sep. 3, 2003

(65) Prior Publication Data

US 2004/0054935 A1 Mar. 18, 2004

Related U.S. Application Data

(63) Continuation-in-part of application No. 10/159,489, filed on May 31, 2002.

(60) Provisional application No. 60/349,883, filed on Jan. 18, 2002, provisional application No. 60/408,689, filed on Sep. 5, 2002.

(51) Int. Cl.
*G06F 12/14* (2006.01)
*H04L 9/00* (2006.01)

(52) U.S. Cl. .................... 726/5; 726/27; 713/165; 713/193

(58) Field of Classification Search ............... None
See application file for complete search history.

(56) References Cited

U.S. PATENT DOCUMENTS

| 5,434,920 | A | * | 7/1995 | Cox et al. ................... 713/153 |
| 5,638,513 | A | * | 6/1997 | Ananda ........................ 726/5 |
| 6,076,167 | A | * | 6/2000 | Borza ........................... 726/5 |
| 6,195,699 | B1 | * | 2/2001 | Dennis ........................ 709/229 |
| 6,237,093 | B1 | * | 5/2001 | Vatanen ...................... 713/162 |
| 6,584,097 | B1 | * | 6/2003 | Malik .......................... 709/229 |
| 7,150,017 | B1 | * | 12/2006 | Vogl et al. .................. 709/229 |
| 2002/0004833 | A1 | * | 1/2002 | Tonouchi .................... 709/229 |
| 2002/0052851 | A1 | * | 5/2002 | Berman ....................... 705/64 |

OTHER PUBLICATIONS http://www.personalmd.com/press34_article.shtml, 9 pages, Jun. 8, 2000.

* cited by examiner

*Primary Examiner*—Gilberto Barron, Jr.
*Assistant Examiner*—Laurel Lashley
(74) *Attorney, Agent, or Firm*—Nixon Peabody LLP

(57) ABSTRACT

A system and method for protecting sensitive information, for example, a user's personal information, stored on a database where the information is accessible via a communications network such as the Internet. An exemplary embodiment stores the sensitive information on an off-line server. The off-line server is connected to an on-line server. The on-line server is connected to the user via the Internet. The user interfaces with the on-line server, and at a scheduled time window, the sensitive information is made available to the on-line server by the off-line server. Outside of the time window, none of the sensitive information is kept on the on-line server. Thus by placing the sensitive information on-line for only limited periods of time the risk of compromise to the sensitive information is greatly reduced.

30 Claims, 6 Drawing Sheets

FIG. 6

METHOD AND SYSTEM FOR PROTECTING INFORMATION ON A COMPUTER SYSTEM

CROSS REFERENCES

This application is a continuation in part of and incorporates by reference in its entirety U.S. Utility application Ser. No. 10/159,489 filed May 31, 2002, which claims the benefit of U.S. Provisional Application Ser. No. 60/349,883. This application also claims the benefit of U.S. Provisional Application Ser. No. 60/408,689 filed Sep. 5, 2002.

FIELD OF THE INVENTION

The invention relates generally to the field of computer security, and in particular to providing security for information stored on a computer server.

BACKGROUND OF THE INVENTION

The pervasiveness of the Internet has allowed information to become available to a user anywhere and at anytime. A user can store his/her personal information, for example, an address book and family photos on a Web server and be able to access the personal information from, e.g., a home personal computer (PC) or from a cell phone while on vacation in a foreign country. However, unauthorized users, e.g., hackers, also have an increased opportunity to access the user's personal information to, for example, copy, delete, or modify, the user's information.

Despite the growing number of hackers ranging from mischievous teenagers to hardened criminals, the typical Web site has minimal security. A typical Web site has the user's information stored on an on-line database connected to the Web server. A user accesses his/her data via a user ID and a password. The password file is also stored on the Web server. Both the password file and all the information in the database are vulnerable to a hacker. As users begin to store sensitive information such as credit card numbers or personal medical information, on a Web site, this minimal security is inadequate.

In the case of a person's medical records, there are significant advantages to having a person's medical records available on-line, i.e., accessible on a Web server via the Internet. For example, when a person visits a specialist or a physician that is not adequately familiar with the person's medical history and/or current conditions, treatments and medications, a commercially available service is available that will allow the specialist or physician to receive and review information, including the clinical records that have been prepared by the person's previous or other current health care providers, that could indicate the cause of the current problem, help avoid redundant or unnecessary tests and conflicting or ineffective treatments, and help reduce the possibility of adverse drug reactions. However, a person's medical records are particularly sensitive and patients need to be sure of security measures before their records are available for on-line access. Conventional web servers with their on-line databases and password files provide little assurance that a person's medical records will remain secure.

Therefore what is needed is a computer security system which significantly reduces the risk of unauthorized access via the Internet to sensitive information, for example, a user's personal information and more specifically, to a person's medical records stored in a database.

SUMMARY OF THE INVENTION

The present invention provides a system and method for protecting sensitive information, for example, a user's personal information, stored on a database where the information is accessible via a communications network such as the Internet. An exemplary embodiment stores the sensitive information on an off-line server. The off-line server is connected to an on-line server. The on-line server is connected to the user via the Internet. The user interfaces with the on-line server, and at a scheduled time window, the sensitive information is made available to the on-line server by the off-line server. Outside of the time window, none of the sensitive information is kept in the on-line server nor can the information be accessible from the on-line server. Thus by placing the sensitive information on-line for only limited periods of time the risk of compromise to the sensitive information is greatly reduced.

One embodiment of the present invention provides a method for securing information stored on a computer system. First, a user ID and a personal password are created for a user to access the computer system. Next, an access code is generated in response to the authenticated and authorized user scheduling a start time and duration at which to access the information on the computer system. At least at the scheduled start time, the computer system receives the access code and personal password from the user, and responsive to the access code and personal password, the computer system allows the user to access the information for the duration.

Another embodiment of the present invention provides a security system for protecting information stored on a database. The security system includes: a first server computer having the database; a second server computer connected to the first server computer by a first communications path; a user computer connected to the second server computer by a second communications path, where the user computer's only connection to the database is via the second server computer; and an access code generated by the first server computer in response to an authenticated and authorized user scheduling a start time and a duration to access the information on the database. In response to receiving the access code at or after the scheduled start time from the user computer, the first server computer copies a portion of the information to the second server computer, and the copied portion is made accessible to the user via the user computer.

A further embodiment of the present invention includes a security system for protecting information stored on a database. The security system includes: a first server computer having the database; a second server computer connected to the first server computer by a first communications path; a user computer for a user to access the information, where the user computer is connected to the second server computer by a second communications path, and wherein the user computer's only connection to the database is via the second server computer; a phone system, including a telephone connection to the user and a third communications path to the first server computer; and an access code generated by the first server computer after a request by the user via the phone system, where the user enters the access code into the user computer to access the information.

An aspect of the present invention includes a method for providing security for information stored on a first server system, where the first server system is connected to a second server system, and where the second server system is connected to a user computer. First, the first server system generates a code in response to a user scheduling a time period to access information on the first server system and sends the code to the user. At the scheduled time period the second server system receives the code from the user computer system. Responsive to the code, the second server system loads at least part of the information that is stored on the first server system and that has been made available for use by the user computer during the scheduled time period.

Another aspect of the present invention includes a method for accessing information stored on a system having a computer, where the system is connected to a user computer via a communications network. First, a user schedules a time and duration when the user computer is allowed to access information on the system. The scheduling is done via a first communications path of the communications network. Next, an access code is received from the system, where the access code is based on the scheduled time and duration. During the scheduled time period the user computer connects to the system using the access code and a predetermined password. The connecting occurs via a second communications path of the communications network, where the second communications path is different from the first communications path. The user computer has access to the information for the time duration.

These and other embodiments, features, aspects and advantages of the invention will become better understood with regard to the following description, appended claims and accompanying drawings.

BRIEF DESCRIPTION OF THE DRAWINGS

FIG. 6 is a display of an example document from a patient's medical records.

DETAILED DESCRIPTION OF THE INVENTION

Figure 1:
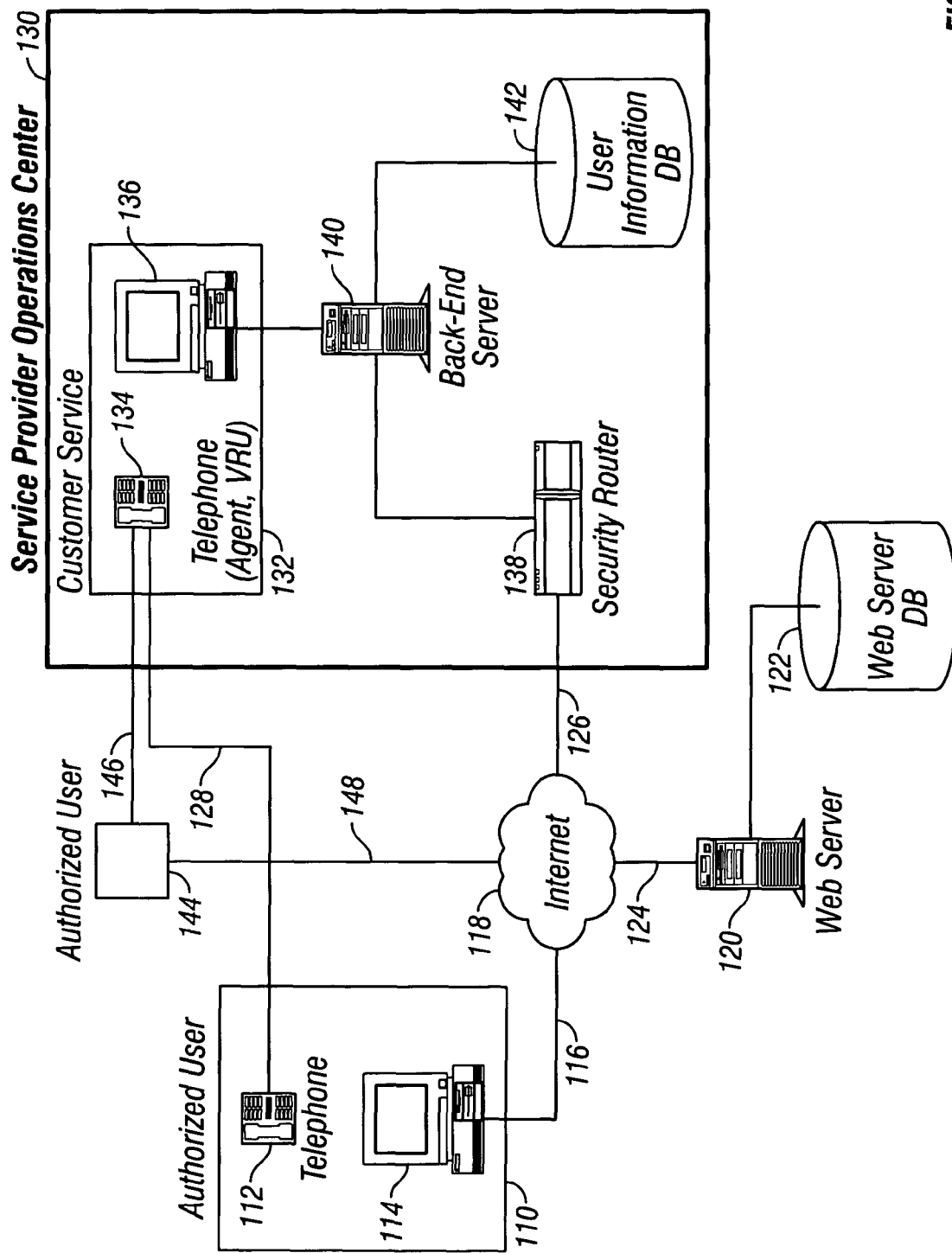
FIG. 1 is a schematic of a client-server security system of one embodiment of the present invention.

In the following description, numerous specific details are set forth to provide a more thorough description of the specific embodiments of the invention. It is apparent, however, to one skilled in the art, that the invention may be practiced without all the specific details given below. In other instances, well known features have not been described in detail so as not to obscure the invention.

One of the major problems with sensitive information located on a Web server is that the sensitive information is continuously on-line, i.e., directly accessible via the Internet, and highly vulnerable to attack by unauthorized users such as hackers. A preferred embodiment of the present invention reduces the risk of comprise by putting the sensitive information on-line only for fixed periods of time called "access periods." The remainder of the time the sensitive information is stored off-line.

One type of sensitive information is a patient's medical records. In one embodiment Internet access to the patient's medical records is restricted to authorized users only during access periods scheduled in advance by the patient or certain other designated users. Scheduling of access periods is performed by a voice telephone request and is therefore independent of the Internet Web Server. The caller making the voice telephone request can be authenticated as an authorized user of the sensitive information by a voice-print recognition process, by a process making use of a telephone-based token, or by traditional combinations of user ID and password. This greatly reduces the possibility of unauthorized access to a patient's medical records by the typical Internet hacking techniques. Further the medical records are not available on the Internet web server until an authorized user logs onto the web server with the appropriate authentication. The information is removed from the Internet web server when the authorized user logs off from the Internet web server (either explicitly logging out or implicitly by not accessing the Internet web server for a specified period of time) or the scheduled time period ends.

In the preferred embodiment of the present invention the security system supports multiple levels of user access. The owner of the medical records, identified as the patient, has the most complete set of rights. The patient can create users with surrogate rights. With the exception of access to certain information designated as private by the patient, surrogate users have the same access rights as the patient. In addition to read access to the medical records, the patient and surrogate user have write access to selected portions of the patient's medical and configuration records. Both the patient and surrogate users have the right to create additional users. The other three types of users are the provider that has write access to selected portions of the patient's medical and configuration records, the provider that does not have such write access, and the limited user. The surrogate, provider, and limited users have read access rights to all medical records except the records that the patient has designated as private records or as records not available to certain levels of user access. Table 1 below summarizes the access rights of each type of user to the patient's medical records. The users for each access level in Table 1, i.e., patient, surrogate, provider with write access, provider without write access, and limited, are all considered authorized users.

TABLE 1

| | Access Rights | | | | |
|---|---|---|---|---|---|
| Access Levels | Assign (create) new users to access patient's account? | Schedule a specific time for viewing patient's medical records online? | Edit patient's records and distribute records to another party? | View patient's "Private" pages? | View patient's non "Private" pages? |
| Patient | YES | YES | YES | YES | YES |
| Surrogate | YES | YES | YES | NO | YES |
| Provider-Level 1 | NO | YES | YES | NO | YES |

TABLE 1-continued

| | Access Rights | | | | |
|---|---|---|---|---|---|
| Access Levels | Assign (create) new users to access patient's account? | Schedule a specific time for viewing patient's medical records online? | Edit patient's records and distribute records to another party? | View patient's "Private" pages? | View patient's non "Private" pages? |
| Provider-Level 2 | NO | YES | NO | NO | YES |
| Limited | NO | NO (*) | NO | NO | YES |

(*) The patient or surrogate user must schedule a session for the limited rights user.

The time during which a patient's medical records are accessible on-line, i.e., the access period, is scheduled by voice and menu-based telephone instructions to a service provider's fully automated voice recognition unit (VRU) or service provider agent. The patient and the surrogate user can schedule access periods for all users in Table 1. The provider can schedule his/her own access period. Access periods for limited-rights users are available only when scheduled by a patient or a surrogate user. Note that a patient's medical records are not on-line during the entire access period, but only need to be on-line when an authorized scheduled user is logged into the Internet Web Server.

FIG. 1 is a schematic of a client-server security system of one embodiment of the present invention. An authorized user 110, having a telephone 112 and a personal computer (PC) 114, is connected to a service provider operations center 130. The service provider operations center 130, includes a customer service center 132 having telephone 134 and PC 136, a backend server 140 with associated user information database (DB) 142, and a security router 138 connected to backend server 140. The backend server 140 is connected to PC 136 in customer service center 132. The authorized user 110 uses telephone 112 to contact the service provider via telephone 134 in customer service center 132 using a public telephone connection 128. A customer service representative of the service provider first authenticates that the caller is an authorized user and then receives the authorized user's scheduling request on telephone 134. Next, using PC 136, the customer service representative schedules a time period on backend server 140 during which the authorized user will be able to access the user information, e.g., a patient's medical records that are stored on user information DB 142. In an alternative embodiment the customer service center is fully automated, using for example a voice recognition unit (VRU), with a voice-print matching process to authenticate the identity of the caller, and menu-based processes for authentication of callers, scheduling of on-line access times, and delivery of session access codes to authorized users. At the scheduled time, the authorized user 110 logs on to Web server 120 using PC 114, where PC 114 is connected to Web server 120 via Internet 118. In the preferred embodiment the Web server DB 120 has only a subset of the user information available, where the subset includes links back to the user information DB 142 for the rest of the user information. In an alternative embodiment a full set of the requested user information, e.g., medical records, is copied from the user information DB 142 to the Web server DB 122. In this embodiment, the backend server 140 initiates the copy process as a result of scheduling instructions received from the customer service center and without any prompts or communications from the authorized user 110 via Internet 118 and security router 138. In yet another embodiment only a subset of user information is on Web server DB 122 and only as a user request more information is the requested information and only the requested information copied to the Web server DB 122 from the user information DB 142. Another authorized user 144 may also schedule an access period with customer service center 132 via telephone 134 and access information at a time scheduled by user 144 on Web server database 122 via Internet 118. Web server 120 and Web server DB 122 are typically operated by the service provider.

In order to increase secure communications, several IP security checks have been implemented. First, only communications between the web server 120 and the backend server 140 are allowed to pass through the security router 138. Second, the backend server 140 only accepts external database requests that originate from the web server 120 IP Address. And third, the web server 120 only accepts schedule requests and user database information from the backend server 140 IP Address.

A significant security feature of an embodiment of the present invention is the use of two separate databases, e.g., web server DB 122 and user information DB 142. The web server database 122 only contains user information required by an authorized user currently logged into the system. The complete database is stored on the user information DB 142. The fact that only a small fraction of the database is stored on the web server 122 for only limited periods of time, significantly reduces the user information that is at risk, if there is a successful unauthorized penetration of the Web Server 120.

Another significant security feature of an embodiment of the present invention is the use of two or more separate communication paths, e.g., a first primary communication path via telephone connection 128 and a separate primary communication path via connection on Internet 118. The first primary communication path is used for authentication of authorized users of specific information that is stored on user information DB 142, and for scheduling time periods to access such information. The first primary communications path, or a secondary communication path, can be used to communicate an access code to the authenticated caller. The access code enables the authorized user to initiate use of a second primary communications path that can access information that has been copied from user information DB 142. A third primary communication path, controlled by the service provider, can be used to schedule the movement information stored on user information DB 142, via the backend server 140, to web server 120 and web server DB 122. The use of multiple communications paths allows for the combination of authentication based on voice communication with Internet-based user access to protected personal or sensitive information. The use of such multiple communication paths, and the associated authentication and information-access processes, make it much more difficult for hackers to obtain unauthorized access to information that can be readily available on the Internet to authorized users. This result is attributable to the fact that many of the methods that could be used by hackers to obtain such unauthorized access to Internet-accessible information become much more complex and difficult to implement successfully in the context of such a multiple-communication-pathway security feature.

The two significant security features described in above paragraphs [0027] and [0028] can each, independently, reduce the risk of unauthorized access to information that, in authorized situations, is readily accessible via Internet 118. In combination the two security features increase the effort required to obtain unauthorized access while at the same time reducing the amount of sensitive information that could be obtained if there were a successful unauthorized penetration of the Web Server 120. By increasing the effort required and also reducing reward obtained, i.e., the amount of information accessed, if there were a successful penetration of Web Server 120, the two security features, working in combination, also reduce the risk that user information will be compromised because they significantly reduce the incentives for hackers that are hoping to benefit economically from their hacking efforts.

Figure 2:
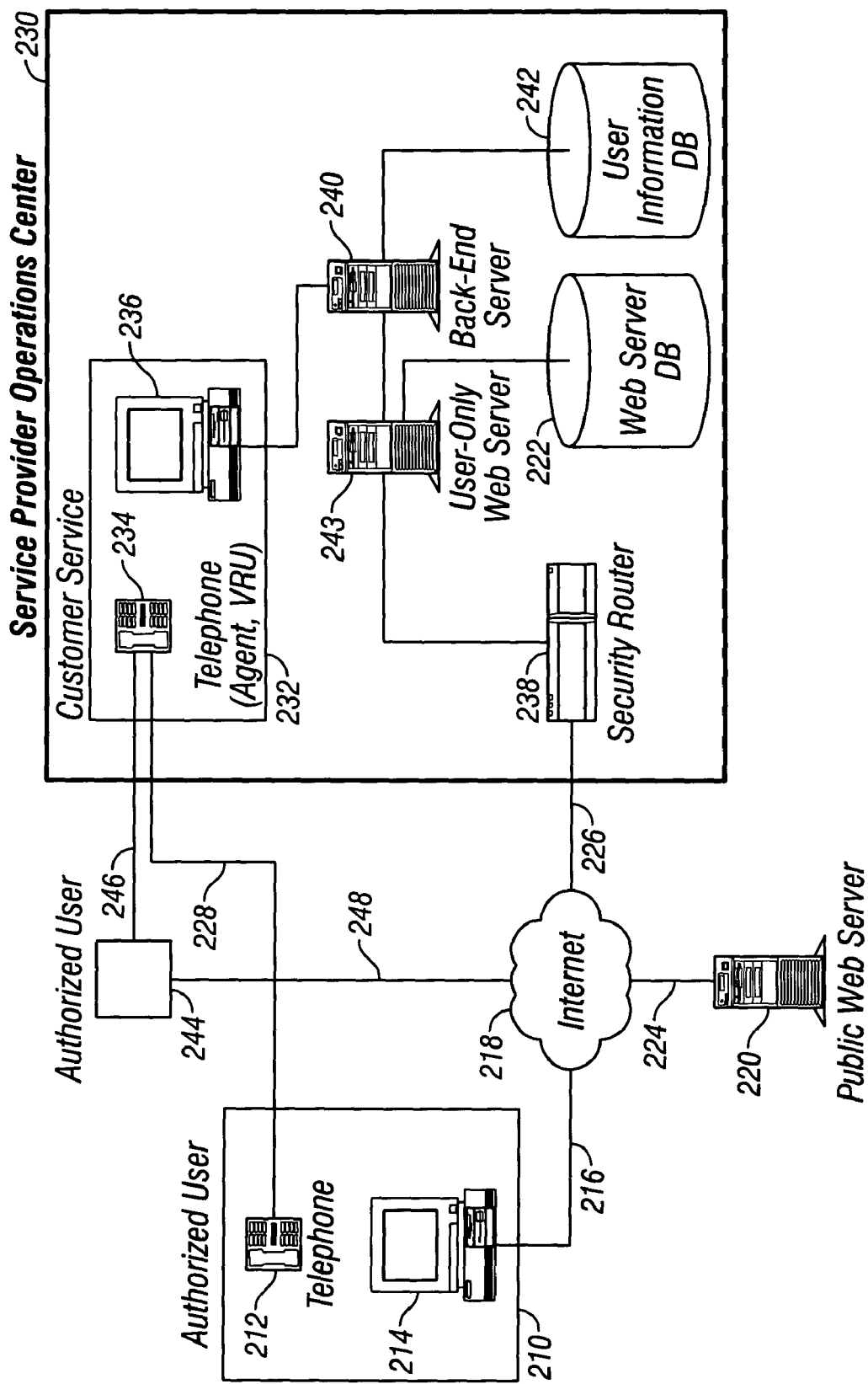
FIG. 2 is a schematic of a client-server security system of another embodiment of the present invention.

FIG. 2 is a schematic of a client-server security system of another embodiment of the present invention. Authorized user 210, having telephone 212 and PC 214, is connected to service provider operations center 230 by a public telephone connection 228 and a separate Internet connection 226, where telephone 212 is connected to telephone 234 equipped with a VRU and PC 214 is connected to security router 238 via Internet 218. The service provider operations center 230, includes a customer service center 232, having telephone 234 and PC 236, a backend server 240 with an associated user information database (DB) 242 connected to customer service center 232, a user-only Web server 243, including associated Web server database 222, connected to backend server 240, and security router 238 connected to the user only Web server 243. Security router 238 is connected via Internet 218 to public Web server 220. Authorized user 210 views publicly available information on public Web server 220. At the scheduled time, when authorized user 210 logs on to public Web server 220 via PC 214, authorized user 210 is re-directed to the user-only Web server 243 which is inside the security router 238. Once logged on, the authorized user 210 communicates directly with user-only Web server 243 and accesses Web server DB 222. Web server DB 222 has available a subset of the user information with the rest of the user information indirectly available on user information DB 242 for the scheduled time period.

Figure 3:
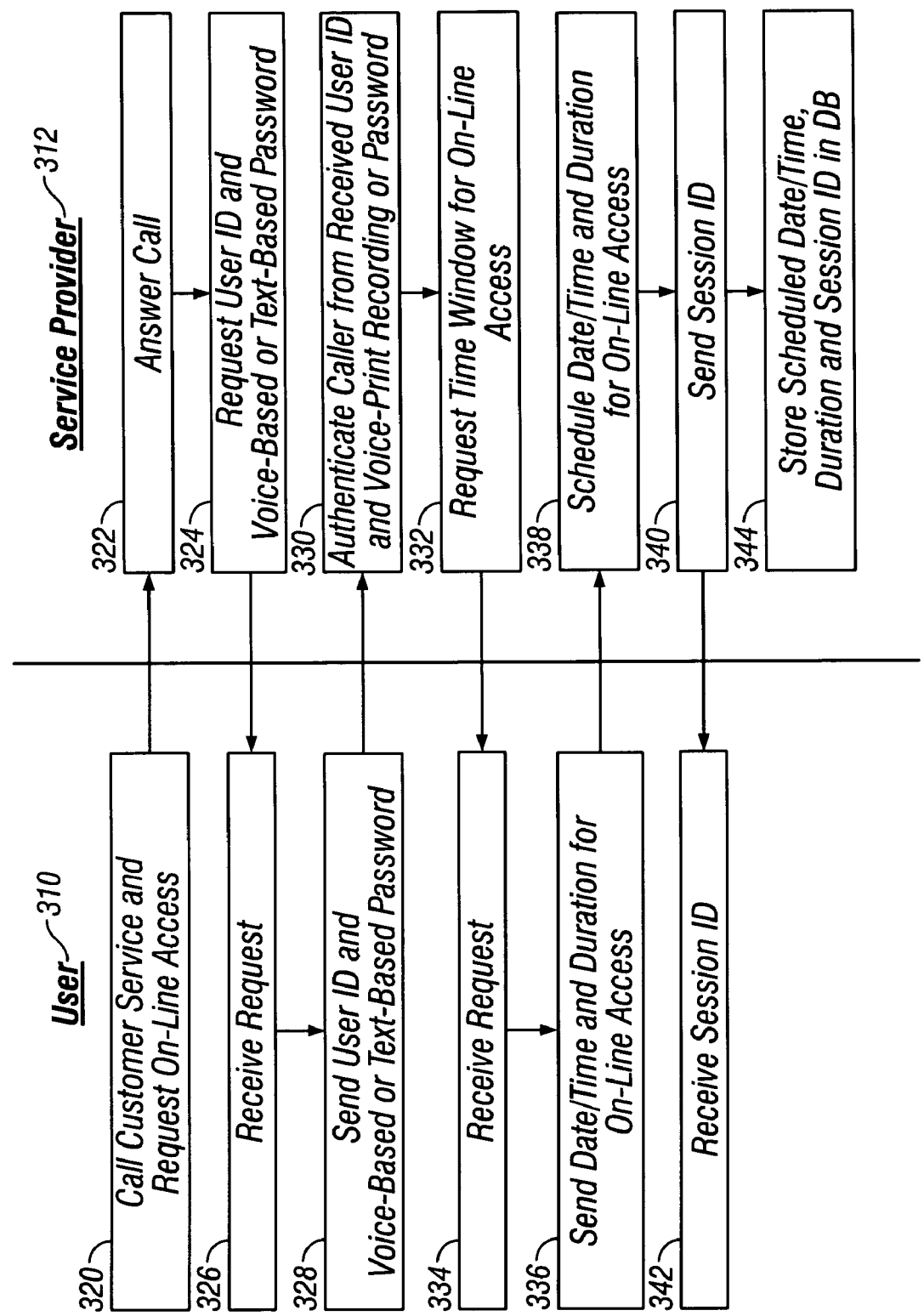
FIG. 3 is a diagram of the process of a user scheduling an access period of an embodiment of the present invention.

FIG. 3 is a diagram of the process of a user 310 scheduling an access period of an embodiment of the present invention. When an authorized user desires access to information stored on backend server user information DB 142 or 242, e.g., a patient's medical records, at step 320, the user 310 calls the customer service center 132 or 232 to request on-line access to the information. In the case of medical records, the user must be a patient, surrogate user, or provider to schedule an access period for on-line access of a patient's medical records. At step 322 the service provider's customer service center 132 or 232 answers the call and requests information to authenticate the caller's authority to access information stored on user information DB 142 or 242 and their authority to schedule information access periods (step 324). The information provided for authentication is used by the service provider 312 to determine the caller's identity, and their authority to access user information and schedule information access periods. The authentication access information can include a user ID (e.g., a patient's service provider member number or a login name) and a previously assigned personal password, or a voice print recorded from the caller that is verified as matching a voice print from user 310 that is already on record with service provider 312. At step 326, the user (e.g., patient, surrogate user, or provider) receives the authentication request and at step 328, sends to the customer service center 132 or 232, the user's ID and requested authentication information. At step 330, the customer service center 132 or 232 authenticates the caller using the user's ID and requested authentication information which should match the user's ID and authentication information stored in the user information database 142 or 242. In the preferred embodiment, a voice-print based authentication process is used, and the caller is prompted or asked to say a name or other word or phrase that will allow the service provider 312 to compare the recorded voice print from the caller to the voice print of the specified user that is already on record with the service provider and stored in the user information DB 142 or 242. In another embodiment, a password-based authentication process is used, and the password match is done by first doing a one way encryption, e.g., using a hash function, of the password and then comparing the encrypted password to a table of encrypted passwords stored in the user information database 142 or 242. The unencrypted passwords are not stored on any of the databases. Hence even if the encrypted password file is stolen, decrypting the file to get the original unencrypted passwords would be extremely difficult. When, at step 330, there is a User ID and voice print match or a User ID and encrypted password match, at step 332 the customer service center 132 or 232 requests a time window for on-line access from the user, which is received at step 334 by the user 310. If the person who is going to view the patient's medical records has limited access, then the patient or surrogate user tells the customer service center the name, i.e., User ID, of the limited user who will access the records at the scheduled time. At step 336 the user sends the access period, i.e., the date/time and duration (and if necessary, limited user name) for on-line access to the customer service center. The customer service center schedules via PC 136 or 236, the date/time and duration (and if necessary, limited user name) for on-line access to user information on Web Server 120 or User-only Web Server 243 (step 338). Backend server 140 or 240 generates a Session ID, i.e., a session access code, and the customer service center sends to the user this Session ID for future use (steps 340 and 342). At step 344 the scheduled date/time, time duration, and session ID are stored in user information DB 142 or 242.

Figure 4:
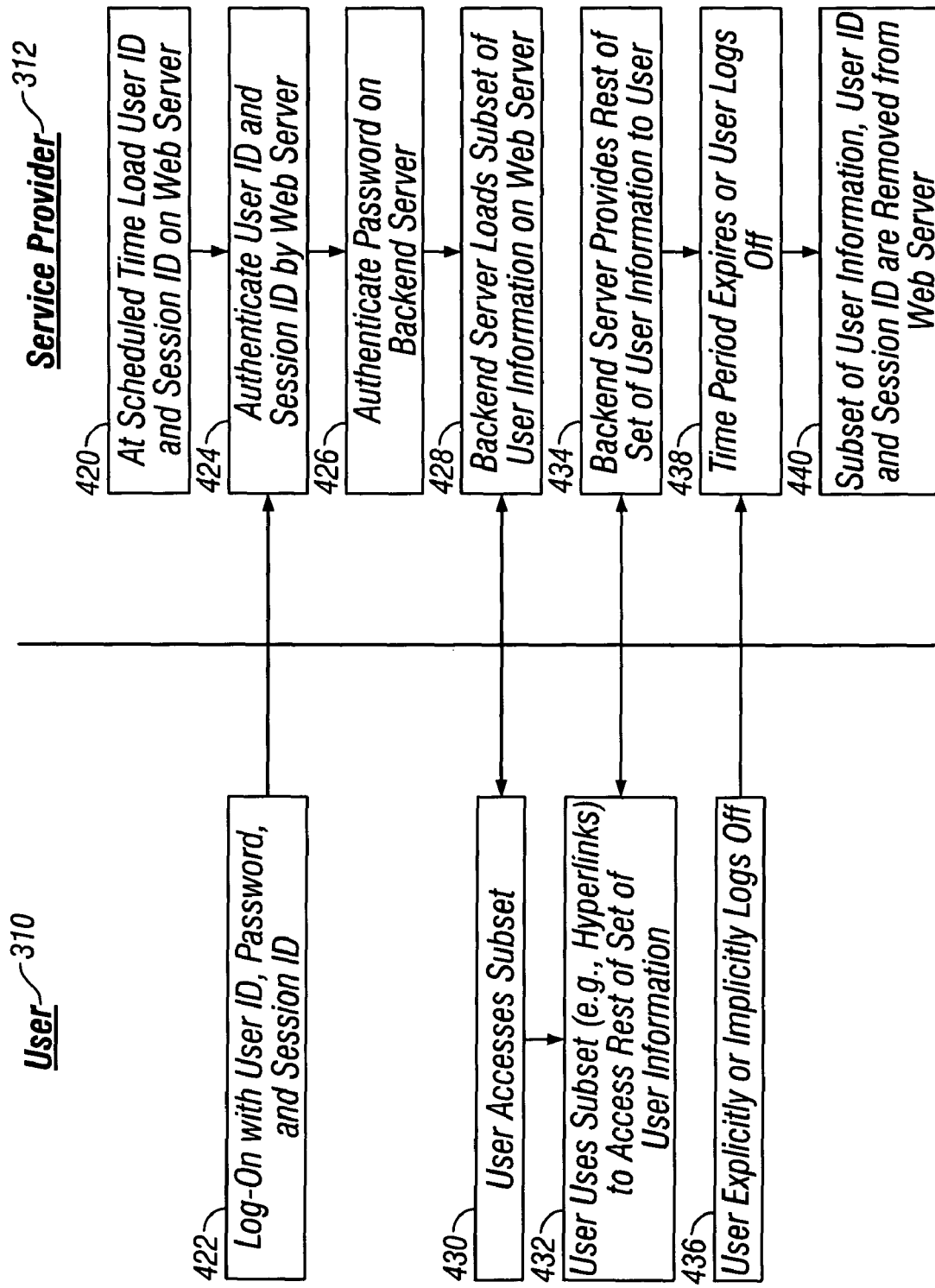
FIG. 4 is a diagram of the process of a user accessing information during the pre-scheduled time period of one embodiment of the present invention.

FIG. 4 is a diagram of the process of a user accessing information during the pre-scheduled time period of one embodiment of the present invention. At step 420 at the scheduled time the backend server 140 or 240 loads the user ID and session ID from the user information database 142 or 242 onto the Web server 120 or the User-only Web server 243. At or after the scheduled time (but before the end of the access period), the authorized user 310 logs on to web server 120 with a user ID, password, and session ID (step 422). At step 424, the Web server 120 or User-only Web server 243 authenticates the user ID and session ID. Upon this preliminary authentication, the password is sent from Web server 120 or User-only Web server 243 to backend server 140 or 240, one-way encrypted, and compared to an encrypted password file by the backend server 140 or 240. Unencrypted passwords are not stored on the servers, e.g., Web server 120 and backend server 140, nor any of the Databases, e.g., DB 122 and 142. In an alternative embodiment the password is encrypted on Web server 120 or User-only Web server 243 before being sent to backend server 140 for comparison. Upon authentication of the password, backend server 140 or 240 loads a subset of the user information from user information DB 142 or 242 onto Web server DB 122 or 222. For example user information DB 142 may have a patient's complete set of medical records which are indexed by a document log. The document log includes hyperlinks to pages in the patient's medical records. In this case, the subset of user information which is loaded on to Web server DB 122 includes the document log. Other subset information may include the patient's name, patient input forms, patient health information summary reports, and clinical summaries of the patient's health collected from the patient's health care providers. At step 432 the authorized user uses the subset, for example, selects a hyperlink in the document log, to access the rest of the set of user information stored in the user information database 142 or 242, for example the scanned medical record page associated with the hyperlink. The backend server 140 or 240 provides the rest of the set of user information when requested by the user, e.g., the user selects a hyperlink (step 434). This indirect access to a user's information on DB 142 or 242 reduces the exposure to hackers compared to the conventional Web server which has the user's information available directly on Web server DB 122. The user may explicitly log off or implicitly log off, i.e., the PC 114 or 214 remains idle for predetermined amount of time (step 436). The backend server 140 or 240 will terminate the connection 126 or 226 when the user explicitly or implicitly logs off or the scheduled time period expires (step 438). At step 440, the subset of user information, the user's ID (including patient's service provider member ID and login name) and session ID are removed from the Web server database 122 or 222.

A significant security feature of the above embodiment of the present invention is that there are two separate codes needed to access the user information: a voice print or a personal password that is user specific and a Session ID which is specific to the particular access period. In addition the communication path, e.g., public telephone path 128, to obtain the Session ID is different than the communication path, e.g., Internet path 116 and 124, to logon to the Web server 120 at the scheduled time. Both of these security measures either alone or in combination significantly reduce the risk of an unauthorized access to user information.

Figure 5:
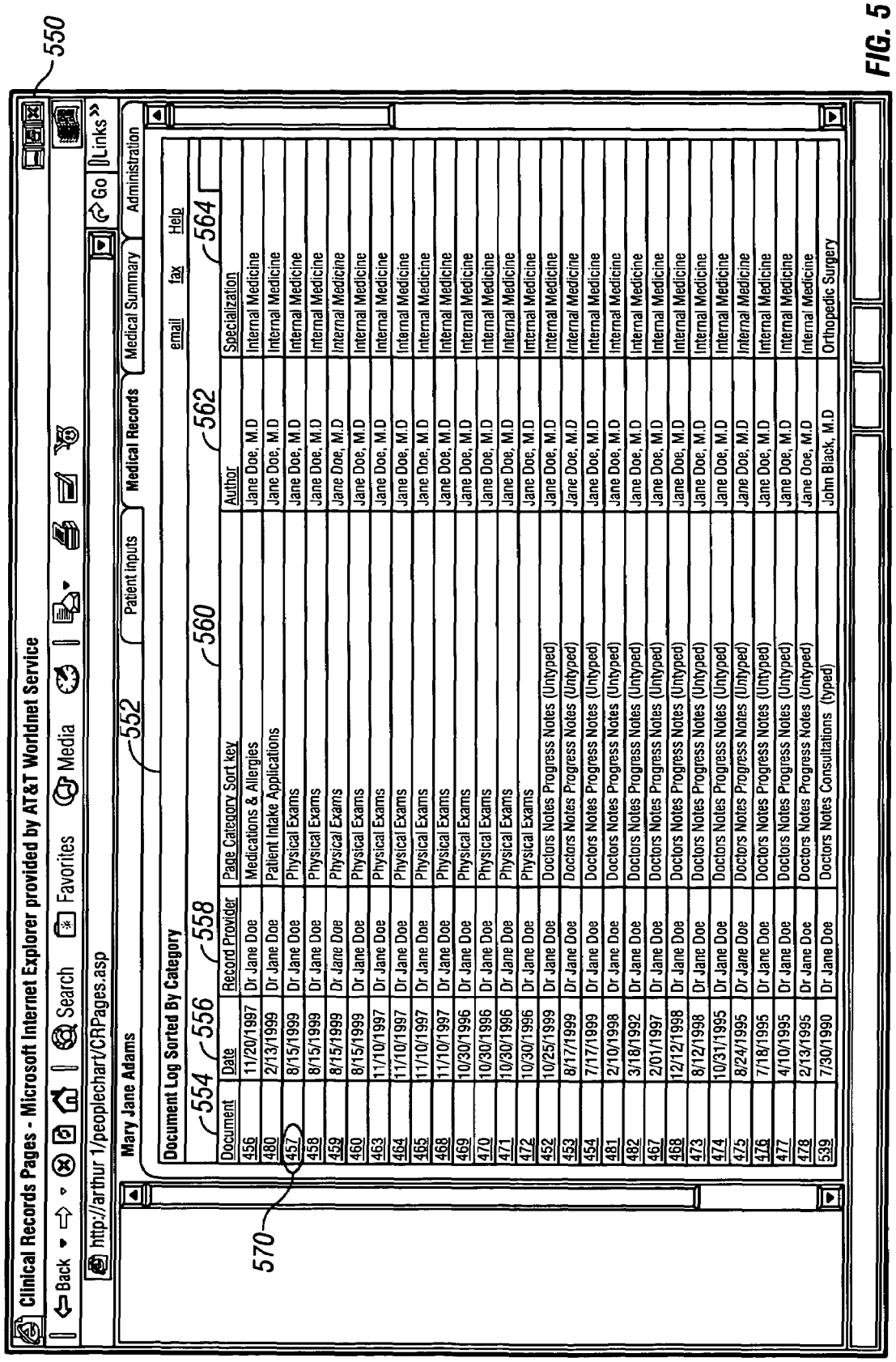
FIG. 5 is an example of a document log sorted by medical sub-category of an embodiment of the present invention.
Figure 6:
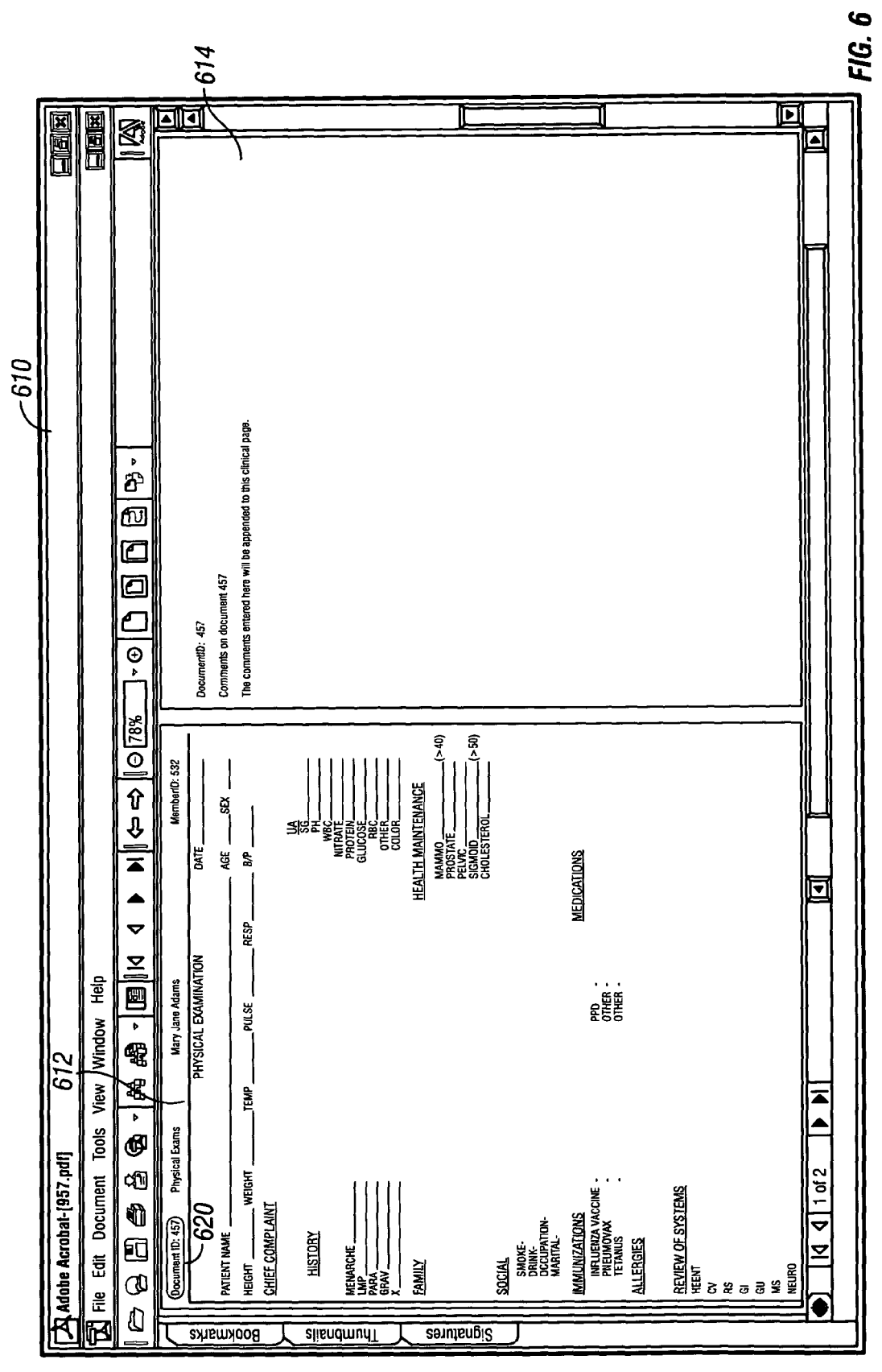

As an example of the subset and set of information stored in the Web server DB 122 and User Information DB 142 during the scheduled access period by a user is illustrated in FIGS. 5 and 6 below. FIG. 5 shows a document log that is loaded as part of the subset of information stored on the Web server DB 122. FIG. 6 shows one of the medical records stored on the user information DB 142 that is displayed on user PC 114, when a hyperlink is selected by the user from the document log.

FIG. 5 is an example of a document log sorted by medical sub-category of an embodiment of the present invention. The pane 552 in window 550 includes the document log sorted by the medical sub-categories, e.g., "Medications & Allergies," "Patient Intake Applications," and "Physical Exams." Column 554 gives the document ID for each document of a patient's medical records stored in user information DB 142. Cell 570 has document ID 457, which is a hyperlink to the document image. When link "457" is selected a separate window (FIG. 6) opens with the document's image. The pane 552 further includes, column 556, which has the date the document was created, e.g., Jun. 15, 1999, column 558, which has the healthcare provider that provided the document, e.g., Dr. Jane Doe, column 560, which has the "Page Category," e.g., medical sub-category and the primary "Sort Key," and in this example, "Physical Exams," column 562, which has the name of the doctor who created the document, e.g., Jane Doe, M.D., and column 564, which has the specialization of the doctor in column 562, e.g., Internal Medicine.

FIG. 6 is a display 610 of an example document from a patient's medical records. The document ID is 457 as shown by label 620. The document includes two parts, the scanned and indexed image of a Physical Exam record 612 and a comment section 614 for patient or doctor comments. The document is displayed when hyperlink "457" 570 is selected in FIG. 5.

Although specific embodiments of the invention have been described, various modifications, alterations, alternative constructions, and equivalents are also encompassed within the scope of the invention. The described invention is not restricted to operation within certain specific data processing environments, but is free to operate within a plurality of data processing environments. Additionally, although the invention has been described using a particular series of transactions and steps, it should be apparent to those skilled in the art that the scope of the invention is not limited to the described series of transactions and steps.

Further, while the invention has been described using a particular combination of hardware and software, it should be recognized that other combinations of hardware and software are also within the scope of the invention. The invention may be implemented only in hardware or only in software or using combinations thereof.

The specification and drawings are, accordingly, to be regarded in an illustrative rather than a restrictive sense. It will, however, be evident that additions, subtractions, deletions, and other modifications and changes may be made thereunto without departing from the broader spirit and scope of the invention as set forth in the claims.

What is claimed is:

1. A method for securing information stored on a computer system, comprising:

creating a user ID and personal password for a user to access said computer system;

generating an access code in response to said user scheduling a future start time and duration to access said stored information on said computer system, wherein an end time comprises said duration added to said scheduled figure start time;

before said end time and at or after said scheduled future start time, said computer system receiving said access code, user ID and personal password from said user; and responsive to said access code, user ID and personal password said computer system, allowing said user to access said stored information for no longer than said duration.

2. The method of claim 1 wherein said access code is generated only after receiving from said user at least said personal password created for said user.

3. The method of claim 1 wherein said personal password is encrypted when received by said computer system and wherein said encrypted password is authenticated using an encrypted password file.

4. The method of claim 3 wherein only said encrypted password file is stored on said computer system and not an unencrypted password file.

5. The method of claim 1 wherein said personal password is associated with said user via said user ID.

6. The method of claim 5 wherein the step of generating said access code is further in response to receipt of said user ID and said personal password.

7. The method of claim 1 wherein said user logs on to said computer system using another computer system connected to said computer system via a communications network.

8. The method of claim 7 wherein said communications network is the Internet.

9. A security system for protecting information stored on a database, comprising:
   a first server computer comprising said database;
   a second server computer connected to said first server computer by a first communications path;
   a user computer connected to said second server computer by a second communications path; and
   an access code generated by said first server computer in response to a user scheduling a future start time and a duration to enable said user computer to access said information on or after said scheduled future start time and for no longer than said duration, wherein an end time comprises said duration added to said scheduled future start time; and
   wherein, responsive to receiving said access code before said end time and at or after said scheduled future start time from said user computer, said first server computer copying a portion of said information to said second server computer, and wherein said user computer has access to said portion of said information only on said second server computer.

10. The security system of claim 9 wherein said second communications path is an Internet path.

11. The security system of claim 9 wherein said access code is received by said user via a third communications path, comprising a public telephone line.

12. The security system of claim 9 wherein said portion of said information comprises a document log, said document log having a hyperlink to a medical record of a patient.

13. The security system of claim 9 wherein said information comprises a user's medical records.

14. The security system of claim 9 further comprising:
   a password for use by said user in accessing said information; and
   an encrypted password file stored on said database for authenticating said user computer by using said password, before said portion of said information is accessible to said user computer.

15. A security system for protecting information stored on a database, comprising:
   a first server computer comprising said database;
   a second server computer connected to said first server computer by a first communications path;
   a user computer for a user to access said information, said user computer connected to said second server computer by a second communications park;
   a phone system, comprising a telephone connection to said user and a third communications path to said first server computer; and
   an access code generated by said first server computer after a request by said user via said phone system to access said information during a future time period, wherein said user enters said access code into said user computer to access said information, and wherein said first server computer copies a portion of said information to said second server computer, and wherein said user computer has access to information in said database only when said information resides on said second server computer.

16. The security system of claim 15 wherein said phone system is fully automated.

17. The security system of claim 15 wherein said phone system further includes a telephone for communicating with said user and a PC for communicating with said first server computer.

18. A method for providing security for information stored on a first server system, said first server system connected to a second server system, wherein said second server system is connected to a user computer, said method comprising:
   said first server system generating a code in response to a user scheduling a future time period to access information on said first server system;
   sending said code to said user;
   at a time in said scheduled future time period, receiving said code by said second server system from said user computer system; and
   said second server system responsive to said code, loading at least part of said information stored on said first server system for use by said user computer until said scheduled future time period ends.

19. The method of claim 18 wherein said scheduling is via a first communications path of said communications network.

20. The method of claim 19 wherein said receiving is via a second communications path of said communications network, wherein said second communications path is different from said first communications path.

21. The method of claim 18 wherein said first server system generating a code in response to a user scheduling a future time period further comprises:
   authenticating said user using a predetermined user ID and a predetermined user password; and
   only after said authenticating, generating said code.

22. The method of claim 18 wherein said first server system generating a code in response to a user scheduling a future time period further comprises:
   authenticating said user using a predetermined user ID and a prerecorded user voice-print; and
   only after said authenticating, generating said code.

23. The method of claim 18 further comprising:
   receiving a predetermined password from said user computer system;
   after receiving said code by said second sewer system from said user computer system, authenticating said code by said second server system;
   encrypting said predetermined password; and
   authenticating said encrypted predetermined password by said first server system, wherein said encrypted predetermined password must be authenticated before said loading at least part of said information stored on said first server system occurs.

24. A method for accessing information stored on a system, comprising a computer, said system connected to a user computer via a communications network, said method comprising:

a user scheduling a future time and duration when said user computer is allowed to access information on said system, said scheduling via a first communications path of said communications network;

receiving from said system an access code, said access code based on said scheduled future time and duration, wherein an end time comprises said duration added to said scheduled future start time;

before said end time and at or after said scheduled future time, said user computer connecting to said system using said access code and a predetermined password, said connecting via a second communications path of said communications network, wherein said second communications path is different from said first communications path; and said user computer having access to said information for no longer than said duration.

25. The method of claim 24 wherein said user scheduling a future time and duration is via a telephone connection to a service provider representative.

26. The method of claim 24 wherein said user scheduling a future time and duration is via a telephone connection to a service provider's automated voice recognition unit (VRU).

27. The security system of claim 15, wherein, responsive to receiving said access code from said user computer, said first server computer copies said portion of said information to said second server computer.

28. The security system of claim 15, wherein, responsive to said request by said user, said first server computer copies said portion of said information to said second server computer.

29. The method of claim 1, wherein said computer system allows said user to access said stored information only until said end time.

30. The method of claim 24, wherein said user computer has access to said information only until said end time.

* * * * *